(12) United States Patent
Stefanchik

(10) Patent No.: US 8,142,356 B2
(45) Date of Patent: Mar. 27, 2012

(54) METHOD OF MANIPULATING TISSUE

(75) Inventor: David Stefanchik, Morrow, OH (US)

(73) Assignee: Ethicon Endo-Surgery, Inc., Cincinnati, OH (US)

(*) Notice: Subject to any disclaimer, the term of this patent is extended or adjusted under 35 U.S.C. 154(b) by 1163 days.

(21) Appl. No.: 11/693,783

(22) Filed: Mar. 30, 2007

(65) Prior Publication Data
US 2008/0242940 A1 Oct. 2, 2008

(51) Int. Cl.
*A61B 1/32* (2006.01)
(52) U.S. Cl. ........ 600/235; 600/203; 600/208; 600/213; 600/229
(58) Field of Classification Search .......... 600/192, 600/201, 203, 206, 208
See application file for complete search history.

(56) References Cited

U.S. PATENT DOCUMENTS

| | | | |
|---|---|---|---|
| 982,232 A | 1/1911 | Bartholomew | |
| 2,767,705 A | 10/1956 | Moore | |
| 3,589,356 A * | 6/1971 | Silverman | 600/7 |
| 5,127,909 A | 7/1992 | Shichman | |
| 5,235,966 A * | 8/1993 | Jamner | 600/204 |
| 5,259,364 A | 11/1993 | Bob et al. | |
| 5,445,644 A * | 8/1995 | Pietrafitta et al. | 606/151 |
| 5,450,843 A * | 9/1995 | Moll et al. | 600/207 |
| 5,522,795 A | 6/1996 | Green et al. | |
| 5,586,968 A | 12/1996 | Grundl et al. | |
| 5,624,381 A | 4/1997 | Kieturakis | |
| 5,658,307 A | 8/1997 | Exconde | |
| 5,836,913 A | 11/1998 | Orth et al. | |
| 5,885,209 A | 3/1999 | Green | |
| 5,931,845 A | 8/1999 | Amyette | |
| 6,007,521 A * | 12/1999 | Bidwell et al. | 604/264 |
| 6,030,365 A | 2/2000 | Laufer | |
| 6,371,968 B1 | 4/2002 | Kogasaka et al. | |
| 6,699,179 B2 | 3/2004 | Wendlandt | |
| 6,971,990 B2 | 12/2005 | Ziegler et al. | |
| 7,189,249 B2 * | 3/2007 | Hart et al. | 606/185 |
| 2001/0044595 A1 * | 11/2001 | Reydel et al. | 604/98.02 |
| 2003/0176884 A1 | 9/2003 | Berrada et al. | |
| 2004/0097996 A1 | 5/2004 | Rabiner et al. | |
| 2004/0143281 A1 | 7/2004 | Hart et al. | |
| 2004/0199052 A1 | 10/2004 | Banik et al. | |
| 2005/0171467 A1 | 8/2005 | Landman | |
| 2006/0069414 A1 | 3/2006 | Imran et al. | |

(Continued)

FOREIGN PATENT DOCUMENTS

EP 0304380 A2 2/1989

(Continued)

OTHER PUBLICATIONS

European Search Report for EP 08 25 2415, mailed Oct. 31, 2008.

(Continued)

*Primary Examiner* — Eduardo C Robert
*Assistant Examiner* — Jerry Cumberledge
(74) *Attorney, Agent, or Firm* — Nutter McClennen & Fish LLP

(57) ABSTRACT

Devices and methods for moving tissue and/or moving the devices relative to the tissue during a surgical procedure are disclosed. The devices and methods disclosed herein can be used in conventional, open surgical procedures, or in minimally invasive surgical procedures, such as laparoscopic and endoscopic procedures. In one aspect, the method can be used to provide an enlarged opening in the stomach wall for transgastric access.

18 Claims, 8 Drawing Sheets

U.S. PATENT DOCUMENTS

| | | |
|---|---|---|
| 2006/0184194 A1 | 8/2006 | Pal et al. |
| 2007/0118167 A1 | 5/2007 | Hart et al. |
| 2008/0045803 A1* | 2/2008 | Williams et al. .............. 600/204 |
| 2008/0243164 A1 | 10/2008 | Stefanchik |
| 2009/0023983 A1 | 1/2009 | Stefanchik |
| 2009/0248055 A1 | 10/2009 | Stefanchik |

FOREIGN PATENT DOCUMENTS

| | | |
|---|---|---|
| EP | 1721561 | 11/2006 |
| EP | 1803389 | 7/2007 |
| WO | WO-0154565 | 8/2001 |
| WO | WO-02/19886 | 3/2002 |
| WO | WO-03039354 | 5/2003 |

OTHER PUBLICATIONS

International Search Report for PCT/US2009/038764, mailed Jul. 15, 2009.

* cited by examiner

METHOD OF MANIPULATING TISSUE

CROSS REFERENCE

This application cross references and incorporates by reference U.S. patent application Ser. No. 11/693,754 entitled: "Tissue Moving Surgical Device" filed in the name of Stefanchik on even date herewith.

FIELD OF THE INVENTION

The present invention relates to surgical devices useful for moving tissue and/or effecting movement of device relative to tissue.

BACKGROUND OF THE INVENTION

Many surgical procedures require the movement or dissection of tissue. Space constraints as well as the relative remoteness of a distal end of a surgical tool from the surgeon can make it difficult to move tissue. In other surgical procedures, particularly in laparoscopic and endoscopic procedures, movement of the surgical device can be challenging because it is located in a relatively constrained space that is remote from the surgeon. Accordingly, there is a need for devices that conveniently and effectively enable the movement of tissue and/or the movement of surgical tools relative to tissue.

SUMMARY OF THE INVENTION

The present invention generally provides devices and methods for moving tissue such as during a surgical procedure. While the devices and methods disclosed herein can be used in conventional, open surgical procedures, they are particularly useful in minimally invasive surgical procedures, such as laparoscopic and endoscopic procedures.

In one aspect, the method comprising the step of providing a first portion of porous material and a second portion of material. The first and second portions of porous material can be parts of a unitary fabric track supported on a substantially rigid insertion body. The first and second portions of porous material can be portions of a fabric track extending along generally opposite sides of a tapered, outer surface of the insertion body. The method also includes the steps of contacting a first tissue site (such as a portion of one organ) with the first portion of porous material, and contacting a second tissue site (such as a portion of another organ) with the second portion of porous material, and moving the first and second portions of porous material along predetermined first and second paths (such as along the sides of outer surface of the insertion body) to provide relative movement of the first and second tissue sites.

In one aspect, the method can be used in providing an opening in an organ, such as by enlarging an incision on the inside of an internal organ such as the stomach. The method can be carried out transorally, such as through an endoscope introduced into the upper GI tract through the mouth. In another aspect, the method can be used to separate (partially or completely) one organ from another.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides devices and methods for moving tissue and/or moving the devices relative to the tissue during a surgical procedure. While the devices and methods disclosed herein can be used in conventional, open surgical procedures, they are particularly useful in minimally invasive surgical procedures, such as laparoscopic and endoscopic procedures. The principles described herein can be applicable to the particular types of tools described herein, and to a variety of other surgical tools having similar functions. In addition, the tools can be used alone in a surgical procedure, or they can be used in conjunction with other devices, such as endoscopes, that facilitate minimally invasive surgical procedures.

Although the invention is described herein with reference to surgical tools such as obturators and dissectors, one skilled in the art will appreciate that the invention can be adapted to a variety of other surgical tools having similar functions. The term "tissue" is used herein in its broad sense and includes any tissue structure within the body, including organs.

A person skilled in the art will also appreciate that the present invention has application in conventional open surgical and minimally invasive instrumentation as well application in robotic-assisted surgery.

Figure 1:
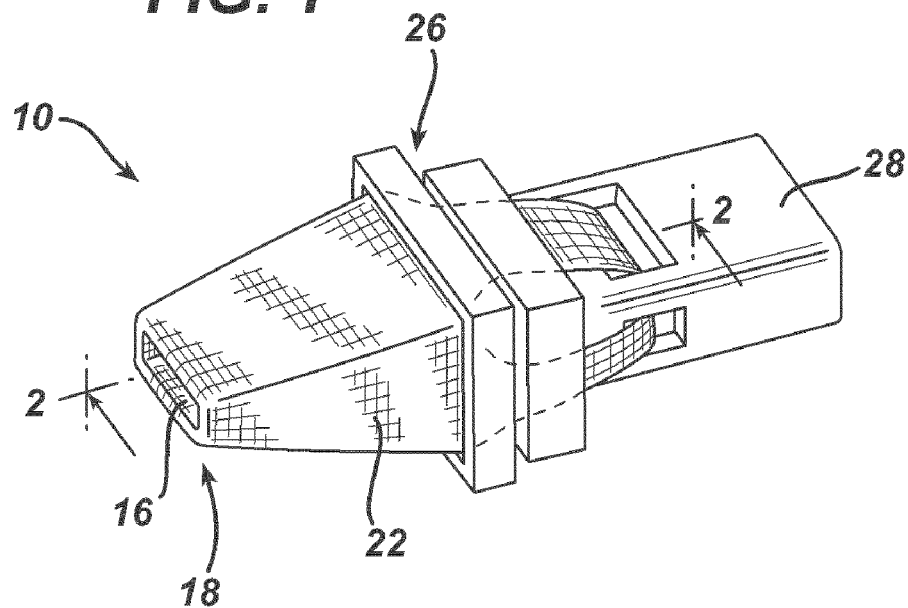
FIG. 1 is an isometric view of a distal end of a tissue moving device according to one aspect of the invention.
Figure 2:
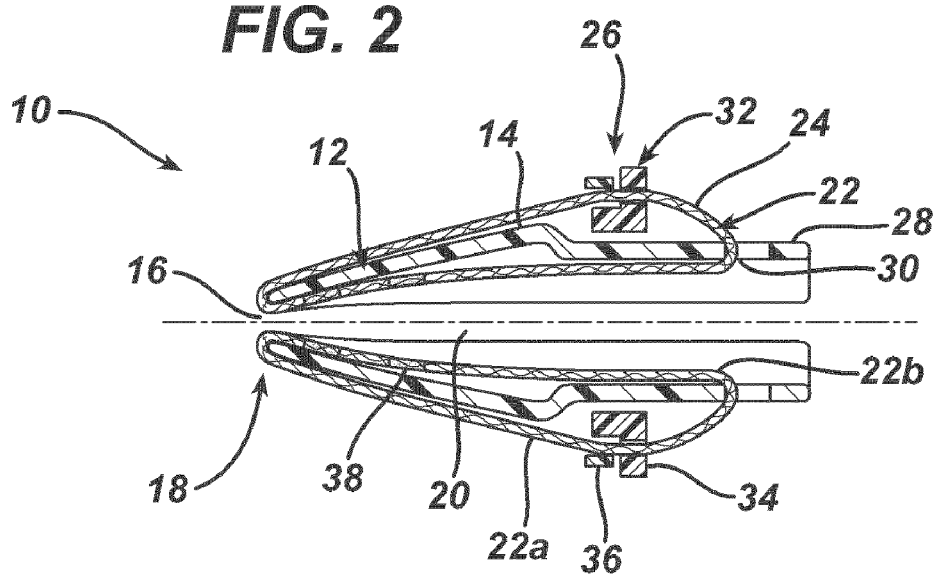
FIG. 2 is a sectional view, at lines 2-2 of the device of FIG. 1 with an actuator in a neutral position.
Figure 3:
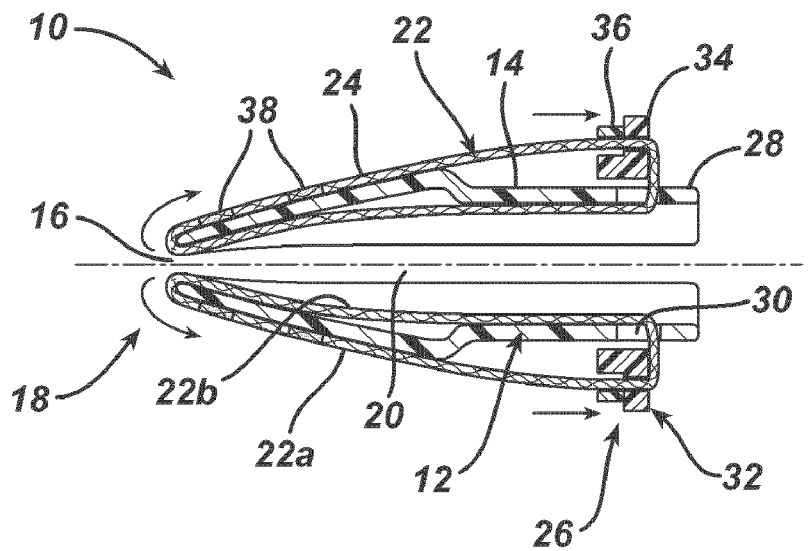
FIG. 3 is a sectional view of the device of FIG. 2 with the actuator in a retracted position.

FIGS. 1-3 illustrate one embodiment of a tissue moving device 10 according to the present invention. The device 10 is a generally elongated member having a substantially rigid body 12 with an outer surface 14 and an opening 16 formed in a distal portion 18 thereof. The opening 16 communicates with a lumen 20 that extends through all or a portion of the body. A fabric material 22 having a tissue contacting outer surface 24 extends over at least a portion of the outer surface 14 of body 12 in such a way that the fabric is configured to be selectively movable relative to the body. The device further includes an actuator mechanism 26 that facilitates the selective movement of the fabric material.

The body 12 may have a variety of shapes that make it useful to access tissue and/or organs within the body. Although only a distal portion of the device 10 is shown in FIGS. 1-3, it is understood that the shaft 28 extending proximally from the distal tip 18 may be of any length that is able to render the device suitable for a variety of surgical procedures, including open, laparoscopic and endoscopic procedures. The distal tip 18 can have a tapered shape, such as that of a wedge, a cone, or a truncated cone that renders it able to be placed at a narrow opening, a tissue interface, or a junction between tissue or organ structures, so as to act in the manner of a wedge. Alternatively, the device can have a generally cylindrical shape. The dimensions of the device 10, particularly its distal tip, will vary depending upon the intended surgical technique and application.

The opening 16 may be formed in a distal facing end of the distal tip 18 of the device (as shown in FIGS. 1-3) or it may be formed adjacent to or in the vicinity of the distal facing end. In any event, the opening 16 should be in communication with the lumen 20 that extends at least partially within the body 12. The body 12 may also have one or more side openings 30 formed in its outer surface 14 to accommodate the fabric material 22 (as explained below).

The fabric material 22 can be virtually any material that is biocompatible, having properties that enables an outer surface 24 of the fabric to contact tissue in such a way that it is able to gain a sufficient traction to enable the contacted tissue and/or the device to move as a result of movement of the fabric. In one embodiment, the fabric material is a porous material such as a mesh material, which can be woven or non-woven. The material from which the mesh is formed can include a variety or synthetic and non-synthetic materials. Examples of synthetic materials include polymers, such as polypropylene, polyethylene, polyester, polytetrafluoroethylene, and nylon. Examples of non-synthetic mesh materials include, but are not limited to silk, cotton, and stainless steel.

Suitable mesh materials can have a number of useful properties. One particularly useful property of the material is that it possess a high coefficient of friction such that it should be able to resist sliding relative to tissue that it contacts. That is, the movement of a low friction mesh material in contact with tissue should result in the tissue moving as a result of the fabric moving.

In one example, the mesh material can be made from a number of cords of fiber that are spaced apart from each other and connected at various points of intersection. Each cord can be formed from a plurality of fine denier filaments that are bundled together, such as by braiding, twisting or weaving.

Suitable mesh materials also tend to have a relatively high porosity as a result of having a high density of holes per square inch. For example, the mesh can have in the range of about 5 to 300 holes per square inch, or preferably, in the range of about 10 to 200 holes per square inch, or more preferably, in the range of about 15 to 30 holes per square inch. Further, the size of the holes in the mesh can vary, but they are typically in the range of about 0.002 to 0.020 inch.

One example of a suitable mesh material is a 4 mm 100 dtex, 16 needle DYNEEMA tube available from Biomedical Structures LLC of Warwick, R.I.

The fabric material can be mounted to the surface of the rigid body 12 in a number of ways, as long as it is able to be selectively moved relative to the body 12. In one embodiment, as illustrated in FIGS. 1-3, the mesh is formed over the outer surface 14 of the body 12 and it extends through opening 16 into lumen 20 and out of a side opening 30. In one aspect the fabric may extend over a part of the surface of the body, such as only a top surface. More typically, however, the fabric 22 extends over virtually the entire outer surface 14 of the body 12 as illustrated.

The connection of the fabric 22 to the body 12 can be accomplished in a variety of ways to enable it to encompass virtually the entire outer surface 14 of the body. In one embodiment, the fabric 22 can be in the form of a tube that is placed within the lumen 20 and then everted such that it extends from within the lumen, out of opening 16 and in through side openings 30 such that the ends of the fabric are joined to each other and/or to an actuator mechanism. The resulting configuration is as shown in FIGS. 1-3. With this type of construction, the fabric resembles a type of tread on the outer surface of the body, enabling it to move relative to the outer surface of the body as will be described below.

The actuation mechanism 26 can be of virtually any design that enables the fabric to be moved selectively relative to the outer surface of the body. In one embodiment, illustrated in FIGS. 1-3, the actuation mechanism 26 may be in the form of an annular ring assembly 32 attached to an outer segment 22a of the fabric. One skilled in the art will appreciate that in the form of what is essentially a tread or continuous loop, the fabric will at any given state of movement have an outer segment 22a disposed adjacent to the outer surface 14 of body 12, which is able to engage tissue, and an inner segment 22b, which is disposed within the lumen 20.

The ring assembly 32 can have a sliding ring component 34 and a locking ring component 36. As shown in FIG. 2, the locking ring component 36 is in the open position such that movement of the sliding ring component 34 will not effect movement of the fabric 22. However, when in the locked position, as shown in FIG. 3, the locking ring component 36 secures the fabric to the slidable sliding ring component 34 such that movement of the ring assembly 32 will cause a corresponding movement of the fabric. As illustrated in FIGS. 2 and 3, the inner segment 22b of the fabric can include markings 38 that are effective to detect motion of the fabric. In the position shown in FIG. 2, which can be called a neutral position, the markings 38 are disposed within lumen 20. When the ring assembly 32 is moved proximally, to the actuated position shown in FIG. 3, a corresponding proximal movement of the fabric 22 along the outer surface 14 of the body takes place. This movement is evidenced by the fact that markings 38 are positioned adjacent the outer surface of the body 12 and FIG. 3.

One skilled in the art will appreciate that a variety of actuation mechanisms, other than the ring assembly 32, may be used. One skilled in the art will appreciate that the actuation mechanism can be disposed internal to the device, as opposed to external to the device, as shown in FIGS. 1-3. The actuation mechanism can also be an element that is separate from the device rather than coupled to the device as illustrated. One skilled in the art will further appreciate that the actuator mechanism can effect movement of the fabric over the outer surface of the body in either the proximal or the distal direction.

As noted above, FIGS. 1-3 illustrate a distal portion of a device useful in a variety of surgical procedures to move tissue relative to the device and/or to assist in moving the device relative to adjacent tissue. The length and width or diameter of the shaft 28 will generally determine the type of surgery for which the device is best suited. For example, a longer and thinner shaft would typically be present on a device used in minimally invasive surgery while a shorter shaft would be more common for a device intended for open surgery.

A variety of alternative device designs having the same or a similar intended function are described below. Since many of the elements of the devices described below are common to those described above, similar reference numerals will be used. However, a numerical prefix will be used to distinguish features of different embodiments. For example, elements of FIGS. 4-6 will be preceded by the prefix "1," the elements of FIGS. 7-8 will be preceded by the prefix "2," and the elements of FIGS. 9-12 will be preceded by the prefix "3." One skilled in the art will appreciate that the structure and function of similarly referenced elements will be substantially the same as described above with respect FIGS. 1-3 except as otherwise noted.

Figure 4:
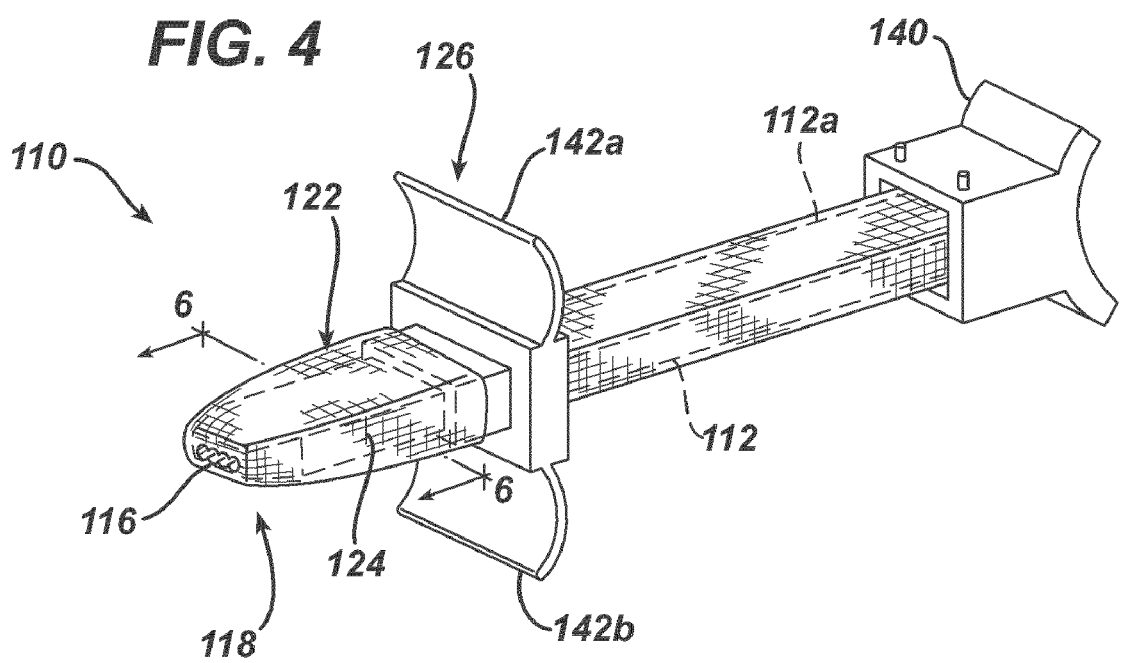
FIG. 4 is an isometric view of another embodiment of a tissue moving device according to the invention in a first position.
Figure 5:
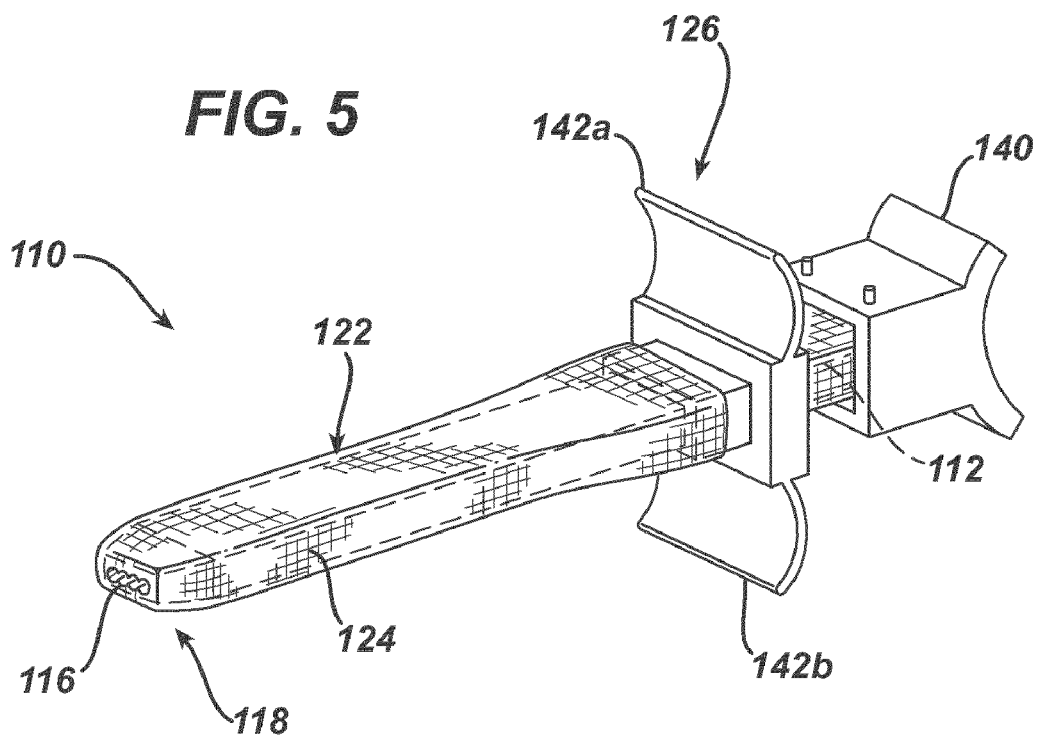
FIG. 5 is an isometric view of the device of FIG. 4 in a second position.
Figure 6:
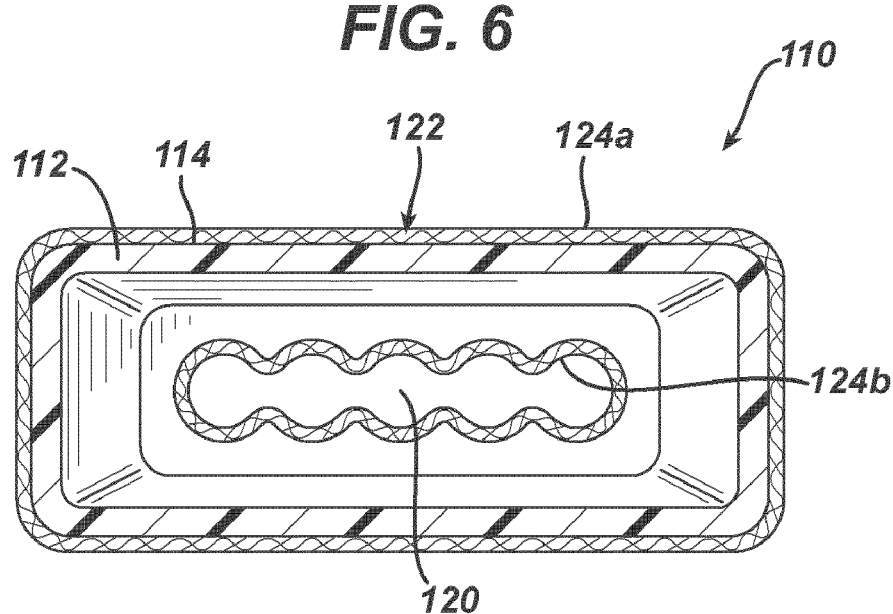
FIG. 6 is a sectional view of the device of FIG. 4 at lines 6-6.

FIGS. 4-6 illustrate another embodiment of another tissue moving device 110 according to the present invention, which also can act as an obturator or dissector that can be used in surgical procedures. FIGS. 4-6 represent a device that can be used in open surgical procedures. As illustrated, device 110 is in the form of a substantially rigid body 112 having an outer surface 114. An opening 116 is formed in a distal portion 118 of the body and the opening communicates with a lumen 120 (FIG. 6) that is formed within all or a part of the rigid body. A proximal portion 112a of the rigid body may include a structure, such as handle 140 that enables the device to be grasped and manipulated. Further, an actuation mechanism 126 having flange components 142a, 142b may be slidably disposed on the rigid body 112 as shown in FIGS. 4 and 5.

Like the device described in FIGS. 1-3, the fabric material 122 of the device of FIGS. 4-6 can be formed on just one portion, e.g., a top portion, of the outer surface 114, or it can envelope substantially the entire outer surface 114 of the rigid body 112. In one embodiment, the fabric material is in a substantially tube-like configuration within the lumen 120 (as shown in FIG. 6) and it extends out of the opening 116 around the outer surface 114 of the rigid body, as shown in FIGS. 4 and 5, where it attaches to a portion of the actuator mechanism 126. Accordingly, the fabric 122 has an outer surface 124a and an inner surface 124b. The distal tip 118 of body 112 can be wedge-shaped to facilitate placement of the device in small openings or at tissue or organ junctures or interfaces.

The principles of operation of the device 110 are similar to those of the device 10. That is, as shown in FIG. 4, the actuation mechanism 126 is in an initial position in which it is disposed towards the distal end of rigid body 112. FIG. 5 illustrates a second position in which the actuator mechanism 126 is retracted proximally. Upon proximal retraction of the actuator mechanism, the fabric 122 on the outer surface 114 of the rigid body 112 moves relative to the rigid body. Thus, when the distal end 118 of device 110 is placed in contact with tissue, such that the tissue is in contact with the outer surface 124 of fabric 122, proximal retraction of the actuator mechanism will cause the fabric to move proximally while at the same time moving the tissue relative to the rigid body as well. Thus, movement of the tissue and/or the rigid body can be effected.

Although the device 110 illustrated in FIGS. 4-6 is of a design that renders it particularly useful for open surgery, it can be adapted for use in other types of surgery such as minimally invasive surgery.

Figure 7:
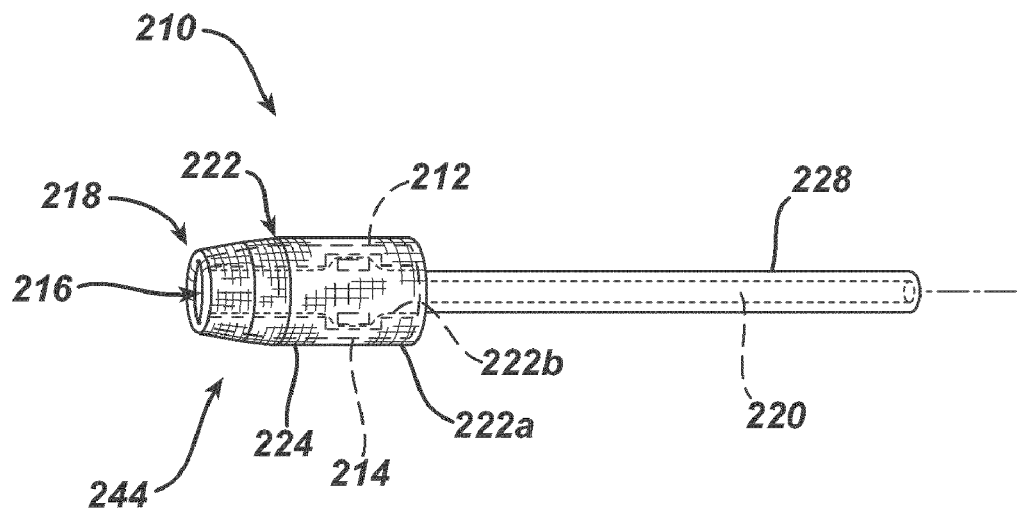
FIG. 7 is an isometric view of a further embodiment of a tissue moving device according to the invention.
Figure 8:
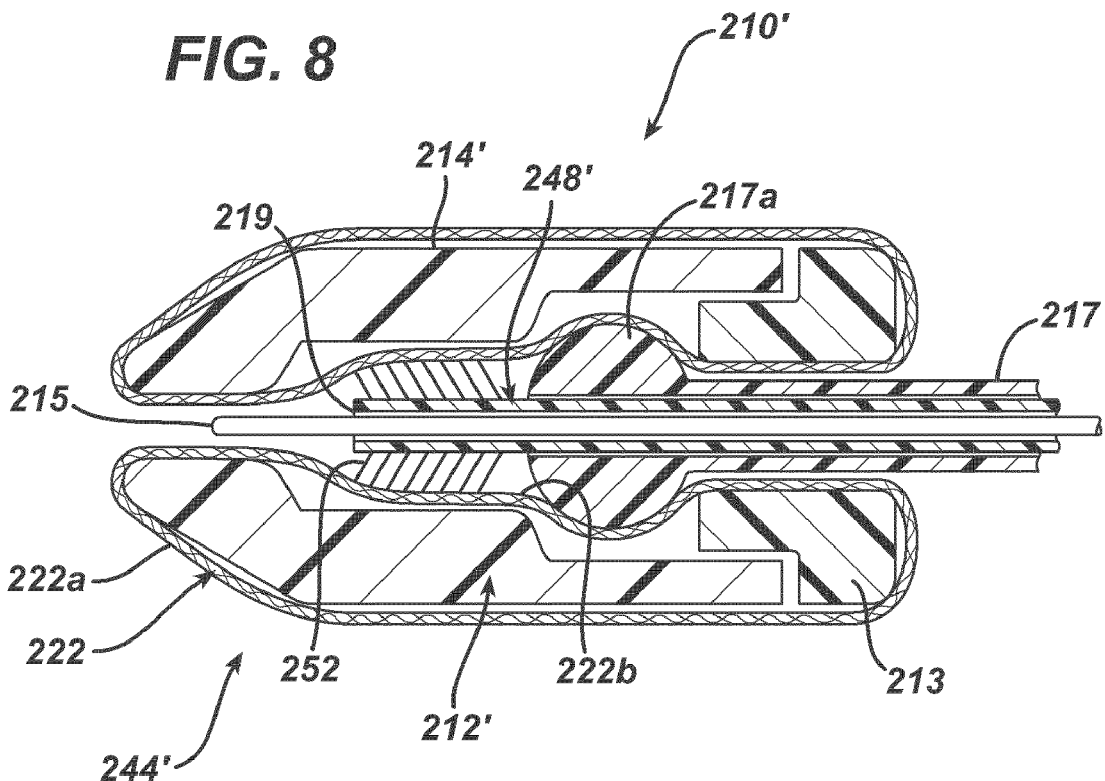
FIG. 8 is a view of a an additional embodiment of a tissue moving device according to the invention.

FIGS. 7-8 illustrate another embodiment of a tissue moving device 210 that is particularly useful in minimally invasive procedures, such as for use with an endoscope.

The device 210 includes an elongated shaft 228 having an end effector 244 in the form of body 212 at a distal end 218 thereof. The end effector 244 can have an opening 216 at a distal end thereof that communicates with the lumen (not shown) that extends through all or part of the end effector. One skilled in the art will appreciate that the lumen can extend around or through the portion of the shaft that is disposed within the end effector. However, it typically extends within the shaft 228 and one or more side openings (not shown) may be formed in the side wall of the shaft in communication with the lumen.

As shown in FIG. 7, a fabric material 222 may extend over at least a portion of the outer surface 214 of the end effector 244. In one embodiment, the fabric 222 may be everted, as described above with respect to FIGS. 1-3, to extend around substantially the entire outer surface of the end effector. In any event, the fabric material 222 should be associated with the end effector 244 in such a way that it is able to selectively move relative to an outer surface 214 of the end effector 244. As described above with respect to FIGS. 1-6, when the fabric is placed in contact with the tissue or an organ, movement of the fabric relative to the outer surface of the end effector will effect relative movement of the tissue or organ and/or the device 210.

Movement of the fabric material 222 can be effected by an actuator mechanism of the type described above with respect to FIGS. 1-6 that is associated with the device 210. Alternatively, a separate actuator mechanism may be utilized. For example, the actuator mechanism may be in the form of an actuator member 246 of the type illustrated in FIG. 7A. As shown, actuator member 246 is an elongate member having a proximal shaft 248 and a distal actuator structure 250 that is fabric-engaging. The actuator member 246 may be inserted within the lumen 220 to selectively contact and move the fabric 222. In one example, the actuator structure 250 can be in the form of a brush member having bristles 252 that are oriented at an acute angle with respect to the longitudinal axis 254 of actuator member 246. For example, the bristles can be distally oriented or proximally oriented.

In one embodiment, when the bristles are distally oriented, distal movement of the actuator member 246 within the lumen will enable the bristles 252 to contact an inner segment 222b of the fabric 222 and effect proximal movement of the fabric 222 along the outer surface 214 of the device 210 by effectively pulling the fabric 222 proximally along an outer surface of the body 212, around the proximal end of body 212, and back into the lumen 220. Movement of an actuator member 246 with distally oriented bristles in a proximal direction will have no effect on the movement of the fabric. Alternatively, the actuator member 246 can be constructed to have proximally oriented bristles 252. With such a design distal movement of the actuator member 246 within the lumen 220 and in contact with an inner segment 222b of the fabric will have no effect on the movement of the fabric. However, proximal movement of the actuator member 246 while the bristles 252 are in contact with an inner segment of the fabric 222b will effect distal movement of the fabric 222 along the outer surface 214 of device 210.

Figure 7A:
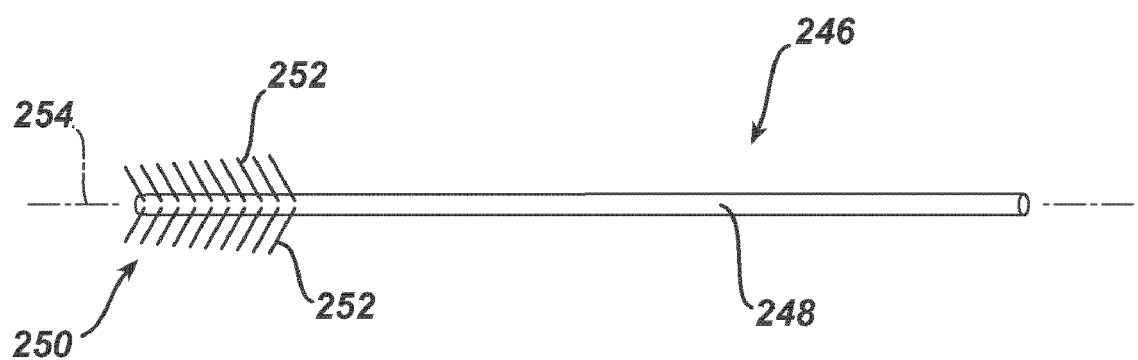
FIG. 7A is an isometric view of an actuator device useful with the tissue moving device of FIG. 7.
Figure 7B:
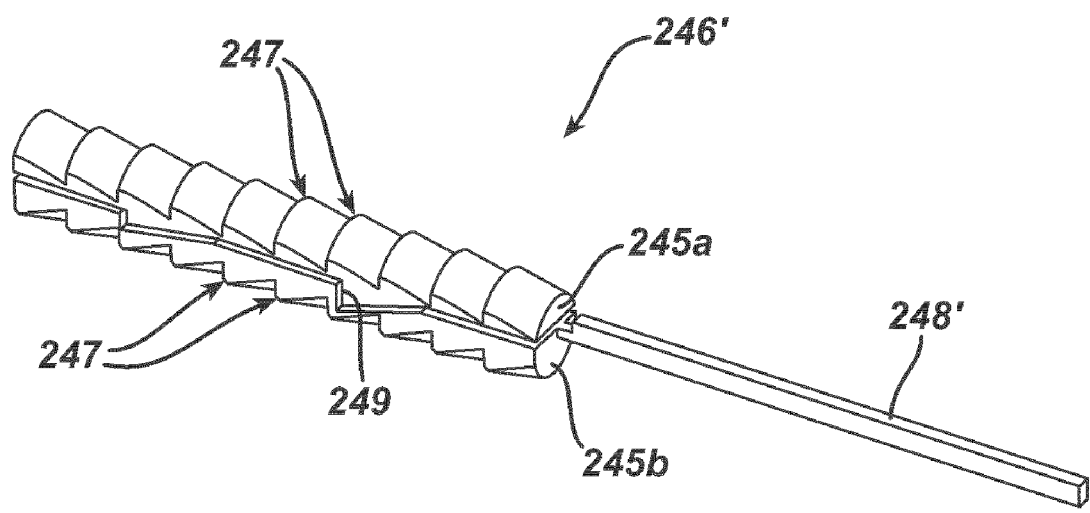
FIG. 7B is an isometric view of an alternative actuator device useful with the tissue moving device of FIG. 7

FIG. 7B illustrates an alternative actuator mechanism 246', which can be used in place of the bristle brush actuator 246 shown in FIG. 7A. As illustrated, actuator 246' is in the form of an elongate member 248' having at a distal end thereof two joined metal half cylinders 245a, 245b. The outer surface of each half cylinder includes teeth 247 while the surfaces where the two half cylinders join includes cam ramps 249. When one half cylinder is pushed distally relative to the other half cylinder, it ramps the other half cylinder to effectively increase the overall diameter of actuator 246' so the teeth can grip the fabric. On the return stroke the cams allow the cylinder halves to collapse the diameter of actuator 246' to ratchet across the fabric without moving the fabric to prepare for the next cycle of fabric movement.

FIG. 8 illustrates a variation of the tissue moving device shown in FIG. 7. The tissue moving device 210', illustrated in FIG. 8, is likewise useful in minimally invasive procedures, such as for use with an endoscope, and it also permits visualization of tissue. Device 210' includes an end effector 244' in the form of a body 212' having a tapered distal end. As shown in FIG. 8, a fabric material 222 may extend over at least a portion of the outer surface 214' of the end effector 244'. In one embodiment, the fabric 222 may be everted, as described above with respect to FIGS. 1-3, to extend around substantially the entire outer surface of the end effector. In any event, the fabric material 222 should be associated with the end effector 244' in such a way that it is able to selectively move relative to an outer surface 214' of the end effector 244'. Like the device described above with respect to FIG. 7, when the fabric is placed in contact with the tissue or an organ, movement of the fabric relative to the outer surface of the end effector will effect relative movement of the tissue or organ and/or the device 210'. An actuator 248' with bristles 252 of the type described above with respect to FIG. 7A can be used to selectively move the fabric relative to the outer surface 214'. A locking cap 213 can be used to lock the position of the fabric. As shown in FIG. 8, the locking cap 213 cooperates with a smooth, enlarged feature 217a formed at a distal end of a shaft 217 that extends within the body 212'. In one embodiment, the shaft 217 includes a lumen formed therein through which the shaft of the actuator 248' may extend. Shaft 248' also includes a lumen 219 formed therein that is sized and configured to receive another instrument 215 such as a guidewire, a needle, and/or a miniaturized visualization device such as a camera.

This embodiment is useful in that the miniaturized visualization device can be an angioscope (e.g., having an outer diameter of about 0.035 inch) that enables a user can to view separation of tissues. This may be useful when using the device to gain access through an organ wall so that the user knows when penetration has occurred and can safely stop the actuation of the device. The lumen 219 can also serve as a space through which to insert a guidewire (not shown), which will act as a placeholder in the opening so that other devices (e.g., dilators, balloons, cannulas) can subsequently be directed to the newly formed space after the device has been withdrawn.

Figure 9:
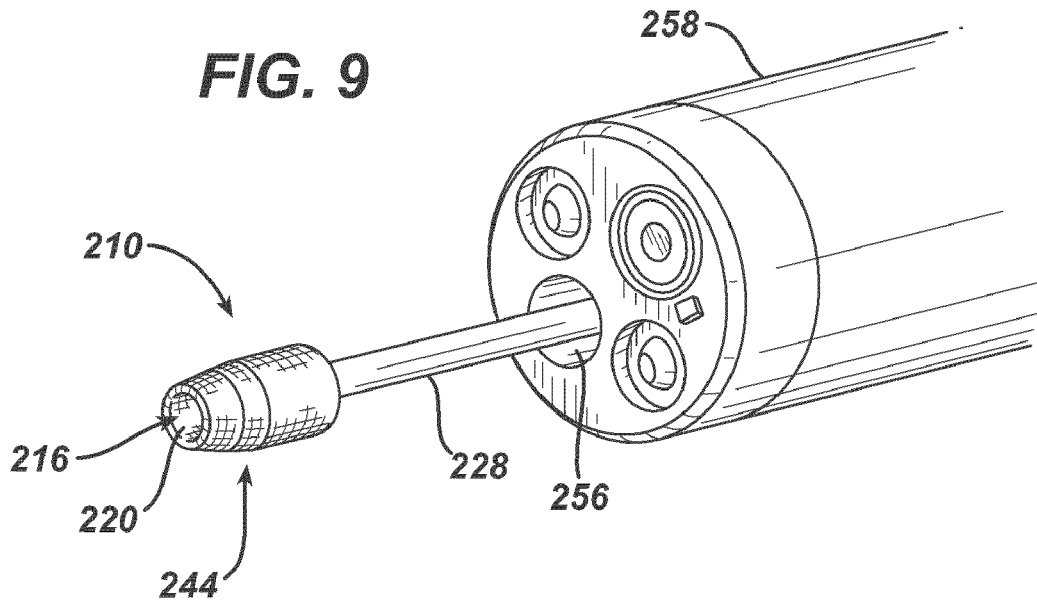
FIG. 9 is an isometric view of a tissue moving device of the type shown in FIG. 7 deployed through an endoscope.

As shown in FIG. 9, the device 210 can be used in minimally invasive surgical procedures. For example, the device 210 can be delivered to a surgical site through a working channel 256 of an endoscope 258 in a manner known to those skilled in the art. In another example, the device 210, or a device of a similar construction with a cylindrical or cone-like distal tip, can be delivered through a blood vessel, such as an artery or a vein.

FIGS. 10-14 illustrate the use of devices according to the present invention in various surgical applications.

Figure 10:
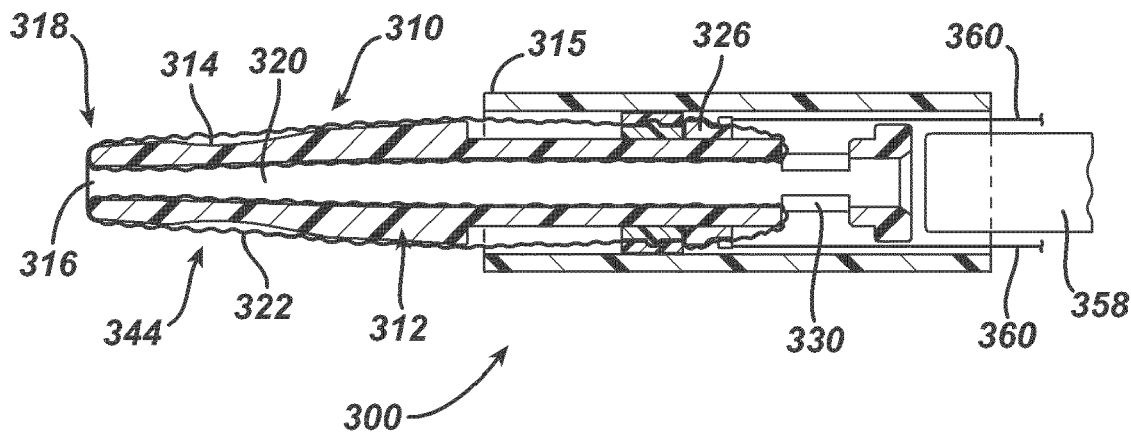
FIG. 10 is a side sectional view of a tissue moving system according to the present invention.
Figure 11:
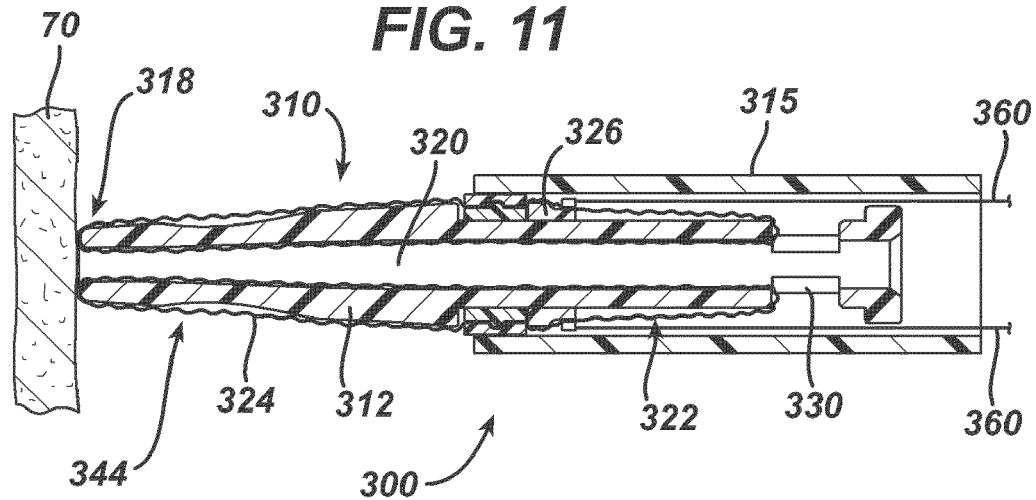
FIG. 11 is a side sectional view of a tissue moving system of FIG. 10 in use in a first position adjacent tissue to be moved.
Figure 12:
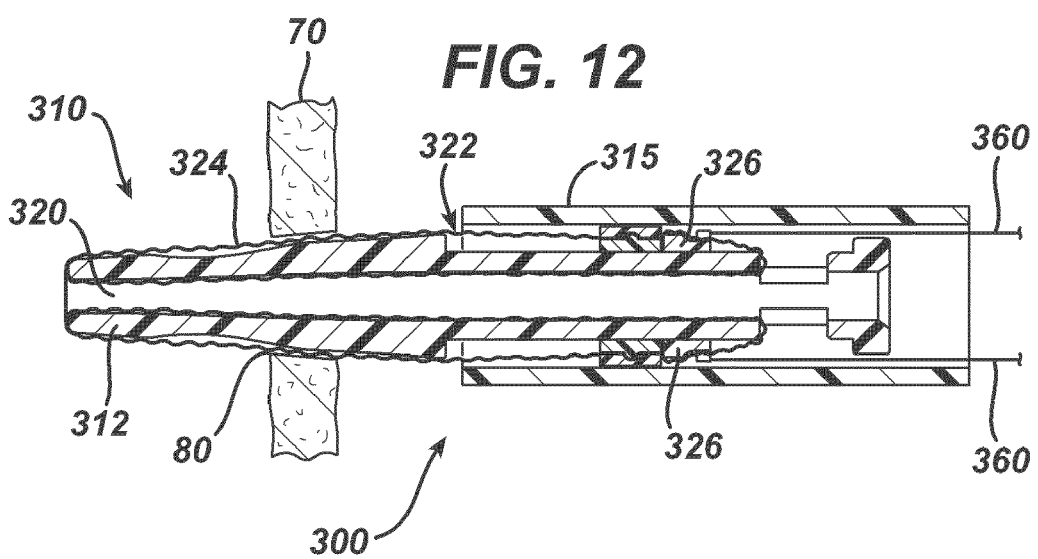
FIG. 12 is a side sectional view of the system of FIG. 10 in a second position adjacent tissue to be moved.

FIGS. 10-12 illustrate the use of a device 310 in an endoscopic procedure involving a system 300 that includes an endoscope 358 and an overtube 315 associated with the endoscope and through which the device 310 is delivered to a surgical site. Device 310 includes an end effector 344 that can be extended beyond the distal end 315 of overtube 314. Device 310 is in the form of a substantially rigid body 312 having an outer surface 314 and an opening 316 formed in a distal portion 318 thereof. The opening 316 communicates with a lumen 320 formed within the rigid body and extending entirely or partially therein. One or more side openings 330 may extend through the outer surface 314 to communicate with lumen 320. As described above with respect to FIGS. 1-9, a fabric material 322 is disposed at least partially within the lumen and extends over at least a portion of the outer surface 314 of body 312. The fabric is attached to an actuator mechanism 326 which can be associated with the device and movable with respect to the outer surface 314 to effect selective movement of the attached fabric 322 relative to outer surface 314, or it can be a separate element. In one embodiment, as shown in FIG. 10, the actuator mechanism 326 may be in the form of a ring or a similar device having a cable 360 attached to one portion, e.g., a proximal portion, of the actuator mechanism 326. The cable can extend through the entire system 300, including the overtube 315, to a proximal end of the system 300 (not shown) such that a user can effect movement of the actuator mechanism and thus the fabric by applying a force, such as tension, to the cable.

In one embodiment, the fabric and the actuator mechanism can be configured such that proximal movement of the actuator mechanism results in proximal movement of the fabric 322 relative to the outer surface 314. Alternatively, and as described above, the system can be configured such that distal movement of the actuator results in movement of the fabric. One skilled in the art will appreciate that more than one actuator can be used and that such multiple actuators can work in concert with each other. For example, one actuator can effectively pull the fabric while another one can effectively push the fabric. One skilled in the art will further appreciate that the actuation mechanism can be biased to one position, such as a forward position, such that following any proximal retraction of the actuator mechanism to effect movement of the fabric, the actuation mechanism will return to its starting position upon the release of tension from cable 360. One skilled in the art will appreciate that the return of the actuation mechanism can be effected manually and/or with the assistance of a biasing mechanism such as a spring.

FIGS. 11 and 12 illustrate the use of devise 310 in an endoscopic surgical procedure in which it is desired to increase the size of an incision in tissue and/or to create such an opening (e.g., a full thickness opening) through which a surgical device can be passed to effect a surgical procedure. The tissue, for example can be the stomach wall, penetration of which is necessary in an endoscopic transgastric surgical procedure.

As illustrated, the end effector 344 is extended beyond a distal and of an over tube 315 such that the distal tip 318 of device 310 adjacent to tissue 70. In an initial position, shown in FIG. 11, a separate surgical device, such as an endoscopic perforator (not shown) is delivered through the endoscope, the working channel, and the device 310 to a position adjacent to tissue 70. A small opening 80 is then made in tissue 70 and the distal tip 318 of device 310 is placed adjacent to the opening 80.

In this position the fabric 322 is in contact with a portion of the tissue 70 adjacent opening 80. Further, the actuator 326 is in a forward position, for example in the vicinity of a distal and of the over tube. Upon a proximal movement of the actuator mechanism 326, for example by applying tension to cable 360, the actuator is retracted as shown in FIG. 12. At the same time, the fabric 322 on the outer surface 314 of rigid body 312 likewise moves proximally with respect to the outer surface 314. This motion, in combination with the wedge-like shape of the end effector 344, causes the size of the opening 70 to increase and it also allows at least a portion of the end effector to move with respect to the tissue such that it extends through the opening 80 and beyond the tissue 70 as shown in FIG. 12.

Thereafter, surgical devices can be delivered through the system 300 to effect a surgical procedure. Alternatively, the opening can be maintained and/or increased by the use of other devices (not shown) and all or part of the system 300 can be removed. If desired, the opening provided can be employed in association with one or more of the methods and devices described in US Patent Application Publication 2004/0260245 published Dec. 23, 2004 in the names of Clem et al, which publication is incorporated herein by reference.

Figure 13:
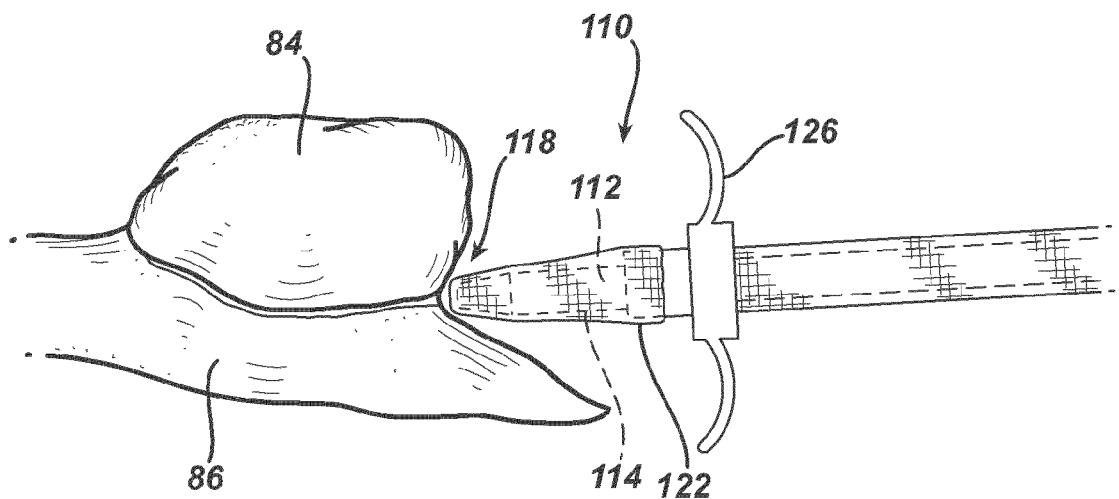
FIG. 13 is a schematic view of a tissue dissector of the type shown in FIG. 4 in use in a first position adjacent tissue layers to be dissected.
Figure 14:
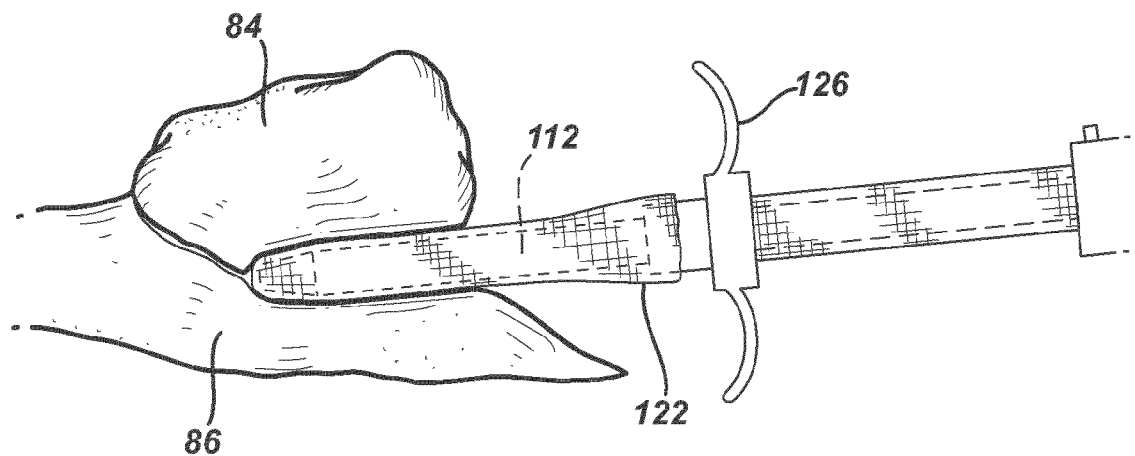
FIG. 14 is a schematic view of a tissue dissector of FIG. 13 in use in a second position between tissue layers being dissected.

FIGS. 13 and 14 illustrate the use of device 110 in a surgical procedure. For purposes of illustration only, the use of device 110 is described with respect to a cholecystectomy and this procedure can be conducted through a conventional open surgical procedure or through a minimally invasive procedure.

As illustrated, the distal tip 118 of device 110 is initially positioned adjacent to a tissue juncture that exists between the gall bladder 84 and the liver 86. With the actuator in the initial, forward position as shown in FIG. 13 a portion of the distal tip 118 can be wedged into the appropriate position. Upon proximal retraction of the actuator mechanism 126, as shown in FIG. 14, the fabric 122 on outer surface 114 of body 112 moves proximally relative to the outer surface 114. This action, combined with the wedge-like shape of the distal tip 118, allows the device 110 to be wedged into the tissue juncture between the gall bladder 84 and the liver 86 to separate these two organs and to facilitate removal of the gall bladder. One skilled in the art will appreciate that such a procedure may require more than one cycle of fabric movement.

One skilled in the art will appreciate that the devices described herein are also amenable to use in a variety of other surgical procedures. For example, the device can be configured for delivery through the vascular system, e.g., through an artery or a vein, to treat a condition of the artery or vein or to access another site in the body where treatment is necessary. As such, the device can be used to remove plaque from an artery or to assist in the removal of plaque, or to perform or assist in the performance of a cardiac procedure. It is further understood that the methods and devices disclosed herein are applicable to use of the device in performing a surgical procedure, as well as to deliver to a surgical site a device or another agent, e.g., a drug.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility. One skilled in the art will appreciate that the device can be sterilized by a variety of other known techniques, including beta or gamma radiation, ethylene oxide, and steam.

One skilled in the art will further appreciate features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for moving tissue, the method comprising the steps of:
    delivering to a surgical site a tissue moving device having a first portion of porous material, a second portion of porous material, and an actuator mechanism that is cyclically movable between a locked position in which the actuator mechanism is engaged to the first and second portions of porous material such that movement of the actuator causes movement of the first and second portions of porous material, and an unlocked position in which the actuator mechanism is disengaged from the first and second portions of porous material and the actuator mechanism is free to move without causing movement of the first and second portions of porous material;
    contacting a first tissue site with the first portion;
    contacting a second tissue site with the second portion;
    moving the actuator mechanism in the locked position to cause the first and second portions of porous material to move along predetermined first and second paths to provide relative movement of the first and second tissue sites.

2. The method of claim 1 wherein the step of providing the first and second portions of porous material comprises providing interconnected first and second portions of porous material.

3. The method of claim 1 wherein the step of providing the first and second portions of porous material comprises providing a continuous track having the first and second portions.

4. The method of claim 1 wherein the step of providing the first and second portions of porous material comprises everting a tubular member formed of porous material.

5. The method of claim 1 wherein the step of moving the actuator mechanism to cause the first and second portions to move comprises driving the first and second portions along the first and second predetermined paths to move the first tissue site away from the second tissue site.

6. The method of claim 5 comprising movably mounting the first and second portions of porous material on an insertion body, and further comprising the step of advancing the insertion body relative to at least one of the first and second tissue sites while driving the first and second portions of porous material along the first and second paths.

7. The method of claim 1 comprising:
disposing the first and second portions of porous material within the stomach;
forming an incision through the stomach;
contacting a first portion of the internal surface of the stomach with the first portions on one side of the incision;
contacting a second portion of the internal surface of the stomach with the second portion of porous material on the other side of the incision; and
moving the actuator mechanism to cause the first and second portions to move and enlarge the incision.

8. The method of claim 1 comprising:
contacting a portion of a first organ with the first portion of porous material;
contacting a portion of a second organ with the second portion of porous material; and
moving the actuator mechanism to cause the first and second portions of porous material to move and separate the first and second organs.

9. The method of claim 1 comprising:
contacting a portion of the gall bladder with the first portion of porous material;
contacting a portion of the liver with the second portion of porous material; and
moving the actuator mechanism to cause the first and second portions of porous material to move along the first and second predetermined paths to separate at least a portion of the gall bladder from at least a portion of the liver.

10. The method of claim 1, further comprising the step of moving the actuator mechanism to the unlocked position to allow repositioning of the actuator mechanism without moving the first and second portions of porous material.

11. A method of forming an opening in a body organ comprising the steps of:
positioning first and second portions of porous fabric within the organ, the first and second portions of porous fabric being movably disposed on a tissue moving device having an actuator mechanism that is cyclically movable between a locked position in which the actuator mechanism is engaged to the first and second portions of porous fabric and an unlocked position in which the actuator mechanism is not engaged to the first and second portions of porous fabric and is able to move without moving the first and second portions of porous fabric;
forming an incision through the wall of the organ;
positioning the first portion of porous fabric to contact the wall of the organ on one side of the incision;
positioning the second portion of porous fabric to contact the wall on the other side of the incision; and
moving the actuator mechanism in the locked position to cause the first and second portions of porous fabric to move relative to one another to enlarge the incision.

12. The method of claim 11 wherein the first and second portions are interconnected prior to the step of positioning the first and second portions within the organ.

13. The method of claim 11 wherein the organ is an internal organ.

14. The method of claim 11 wherein the organ is the stomach.

15. The method of claim 11 wherein the step of positioning the first and second portions within the organ comprises introducing the first and second portions transorally into the organ.

16. The method of claim 11, further comprising the steps of:
repositioning the actuator mechanism while in the unlocked position; and
moving the actuator mechanism while in the locked position to cause further movement of the first and second portions of porous fabric.

17. A method of separating a first organ from a second organ, the method comprising the steps of:
contacting a portion of the first organ adjacent to the second organ with a first portion of porous fabric;
contacting a portion of the second organ adjacent to the first organ with a second portion of porous fabric;
moving the first and second portions of porous fabric along predetermined first and second paths over a substantially rigid insertion body to at least partially separate the first and second organs;
wherein the first organ comprises the gall bladder and the second organ comprises the liver.

18. The method of claim 17 further comprising the step of urging the first and second portions of porous fabric toward a juncture of the first and second organs simultaneously with the step of moving the first and second portions of porous fabric away from each other.

* * * * *